US00RE38143E

(19) United States
(12) Reissued Patent
Tierney et al.

(10) Patent Number: US RE38,143 E
(45) Date of Reissued Patent: Jun. 17, 2003

(54) ORGAN SEPARATION FOR THERMAL THERAPY

(75) Inventors: Mark Tierney, Marietta, GA (US); Richard diMonda, Marietta, GA (US); John Trachtenberg, Toronto (CA)

(73) Assignee: Dornier Medical Systems, Inc., Kennesaw, GA (US)

(21) Appl. No.: 09/767,423

(22) Filed: Jan. 18, 2001

Related U.S. Patent Documents

Reissue of:
(64) Patent No.: 5,733,316
Issued: Mar. 31, 1998
Appl. No.: 08/549,602
Filed: Oct. 27, 1995

(51) Int. Cl.[7] ..... A61N 5/02
(52) U.S. Cl. ..... 607/101; 607/102; 607/113; 607/156
(58) Field of Search ..... 607/100–102, 607/113, 115; 154/6

(56) References Cited

U.S. PATENT DOCUMENTS

| | | | | | |
|---|---|---|---|---|---|
| 5,344,435 | A | * | 9/1994 | Turner et al. | 607/101 |
| 5,385,544 | A | * | 1/1995 | Edwards et al. | 607/101 |
| 5,415,654 | A | * | 5/1995 | Daikuzono et al. | 606/7 |
| 5,428,699 | A | * | 6/1995 | Pon | 606/7 |
| 5,458,612 | A | * | 10/1995 | Chin | 606/192 |
| 5,509,929 | A | * | 4/1996 | Hascoet et al. | 607/101 |

* cited by examiner

*Primary Examiner*—Robert L. Nasser
(74) *Attorney, Agent, or Firm*—Lyon & Lyon LLP

(57) ABSTRACT

A method of providing thermal therapy to prostate tissue of a patient. The method includes: inserting a mechanical separator or infusing a fluid to separate human tissue to be treated from nontarget tissue, thereby providing thermal insulation and other beneficial effects, and applying the thermal therapy to the target tissue.

10 Claims, 5 Drawing Sheets

| BILL OF MATERIALS | | |
|---|---|---|
| ITEM | DESCRIPTION | QTY |
| 10 | OUTER SHAFT SPACER TUBE | 1 |
| 9 | INNER SHAFT SPACER TUBE | 1 |
| 8 | DYMAX UV ADHESIVE | AR |
| 7 | SICORNET ADHESIVE | AR |
| 6 | "Y" BIFURCATE FITTING w/2 FM LUERS | 1 |
| 5 | MALE LUER LOCK | 1 |
| 4 | STRAIN RELIEF | 1 |
| 3 | "Y" BIFURCATE FITTING w/2 FM SLIPS | 1 |
| 2 | 6 F INNER SLEEVE | 1 |
| 1 | 6 F OUTER SLEEVE | 1 |

ORGAN SEPARATION FOR THERMAL THERAPY

Matter enclosed in heavy brackets [ ] appears in the original patent but forms no part of this reissue specification; matter printed in italics indicates the additions made by reissue.

The present invention relates generally to an apparatus and method for performing a thermal therapy patient treatment protocol. More particularly, the invention relates to a novel apparatus and method for physically separating organs to enable aggressive thermal therapy to be administered safely and relatively comfortably, on an outpatient basis, if desired.

Thermal therapy has been proven to be an effective method of treating various human tissues. Thermal therapy includes tissue freezing thermotherapy, hyperthermia treatment and various cooling treatments. Thermotherapy treatment is a relatively new method of treating cancerous, dieseased and/or undesirably enlarged human prostate tissues. Hyperthermia treatment is well known in the art, involving the maintaining of a temperature between about 41.5° through 45° C. Thermotherapy, on the other hand, usually requires energy application to achieve a temperature above 45° C. for the purposes of coagulating the target tissue. Tissue coagulation beneficially changes the density of the tissue. As the tissue shrinks, forms scars and is reabsorbed, the impingement of the enlarged tissues, such as an abnormal prostate, is substantially lessened. Further, tissue coagulation and its beneficial effects are useful for treating cancerous tissue, because cancer cells are particularly susceptible to abnormal temperatures. Cancer cells can be treated in accordance with the present invention with temperatures in excess of 100° C. without damage to the therapy applicator or discomfort to the patient.

The higher temperatures required by thermotherapy require delivery of larger amounts of energy to the target prostate tissues. At the same time, it is important to protect nontarget tissues from the high thermotherapy temperatures used in the treatment. Providing safe and effective thermal therapy, therefore, require devices and methods which have further capabilities compared to those which are suitable for hyperthermia.

Although devices and methods for treating prostate cancer and benign prostatic hyperplasia have evolved dramatically in recent years, significant improvements have not occurred and such progress is badly needed. As recently as 1983, medical textbooks recommended surgery for removing cancerous or impinging prostatic tissues and four different surgical techniques were utilized. Suprapubic prostatectomy was a recommended method of removing the prostate tissue through an abdominal wound. Significant blood loss and the concomitant hazards of any major surgical procedure were possible with this approach.

Perineal prostatectomy was an alternatively recommended surgical procedure which involved gland removal through a relatively large incision in the perineum. Infection, incontinence, impotence or rectal injury were more likely with this method than with alternative surgical procedures.

Transurethral resection of the prostate gland has been another recommended method of treating benign prostatic hyperplasia. This method required inserting a rigid tube into the urethra. A loop of wire connected with electrical current was rotated in the tube to remove shavings of the prostate at the bladder orifice. In this way, no incision was needed. However, structures were more frequent and repeat operations were sometimes necessary.

The other recommended surgical technique for treatment of benign prostatic hyperplasia was retropubic prostatectomy. This required a lower abdominal incision through which the prostate gland was removed. Blood loss was more easily controlled with this method, but inflammation of the pubic bone was more likely.

With the above surgical techniques, the medical textbooks noted the vascularity of the hyperplastic prostate gland and the corresponding dangers of substantial blood loss and shock. Careful medical attention was necessary following these medical procedures.

The problems previously described led medical researchers to develop alternative methods for treating prostate cancer and benign prostatic hyperplasia. Researchers began to incorporate heat sources in Foley catheters after discovering that enlarged mammalian tissues responded favorably to increased temperatures. Examples of devices directed to treatment or prostate tissue include U.S. Pat. No. 4,662,383 (Harada), U.S. Pat. No. 4,967,765 (Turner), U.S. Pat. No. 4,662,383 (Sogawa) and German Patent No. DE 2407559 C3(Dreyer). Though these references disclosed structures which embodied improvements over the surgical techniques, significant problems still remained unsolved.

Recent research has indicated that cancerous and/or enlarged prostate glands are most effectively treated with higher temperatures than previously thought. Complete utilization of this discovery has been tempered by difficulties in protecting rectal wall tissues from thermally induced damage. While shielding has been addressed in some hyperthermia prior art devices, the higher energy field intensities associated with thermotherapy necessitate devices and methods having further capabilities beyond those suitable for hyperthermia. For example, the microwave-based devices disclosed in the above-referenced patents have generally produced relatively uniform cylindrical energy fields. Even at the lower energy field intensities encountered in hyperthermia treatment, unacceptably high rectal wall temperatures have limited treatment periods and effectiveness.

In addition, efficient and selective cooling (for heat-based treatments) or warming (for freezing treatment) of the devices is rarely provided. This substantially increases patient discomfort and increases the likelihood of healthy tissue damage during benign prostatic hyperplasia treatments. These problems have necessitated complex and expensive temperature monitoring systems along the urethral wall. Satisfactory ablative prostate cancer therapy using extremely high or low temperature treatments cannot be undertaken without effective thermal control of the therapy device including effective cooling of exterior portions of the therapy device.

It is therefore an object of the invention to provide an improved apparatus and method suitable for thermal therapy treatment of tissue.

It is another object of the invention to provide an improved method and apparatus for physically separating mammalian organs.

It is yet another object of the invention to provide an improved method and apparatus for physically separating human organs for thermal isolation purposes.

It is a further object of the invention to provide an improved apparatus and method for thermal therapy treatment which separates the prostate from the rectum.

It is yet a further object of the invention to provide a novel method and apparatus for thermal therapy treatment that utilizes a fluid to separate the prostate from the rectum for thermal isolation purposes.

It is a still further object of the invention to provide a novel means for dynamic monitoring of the treatment temperature distribution and to use such information to aid in the control of the deposited power level and its distribution.

It is another object of the invention to provide an improved applicator which can be inserted into a space between a prostate and a rectum and be positioned with respect to the prostate and maintained in position during treatment.

It is a further object of the invention to provide improved control of both power level and the distribution of the power deposited in the prostate in a dynamic fashion during thermal therapy which compensates for physiological changes (temperature, blood flow effects) that can occur during therapy and accommodates operator-desired alterations in the therapeutic energy distribution within the prostate.

It is an additional object of the invention to provide an improved thermal therapy device which minimizes energy reaching the rectal wall in benign prostatic hyperplasia or prostate cancer thermotherapy treatment.

Other advantages and features of the invention, together with the organization and manner of operation thereof, will become apparent from the following detailed description when taken in conjunction with the accompanying drawings, wherein like elements have like numerals throughout the drawings.

DETAILED DESCRIPTION OF PREFERRED EMBODIMENT

Figure 1:
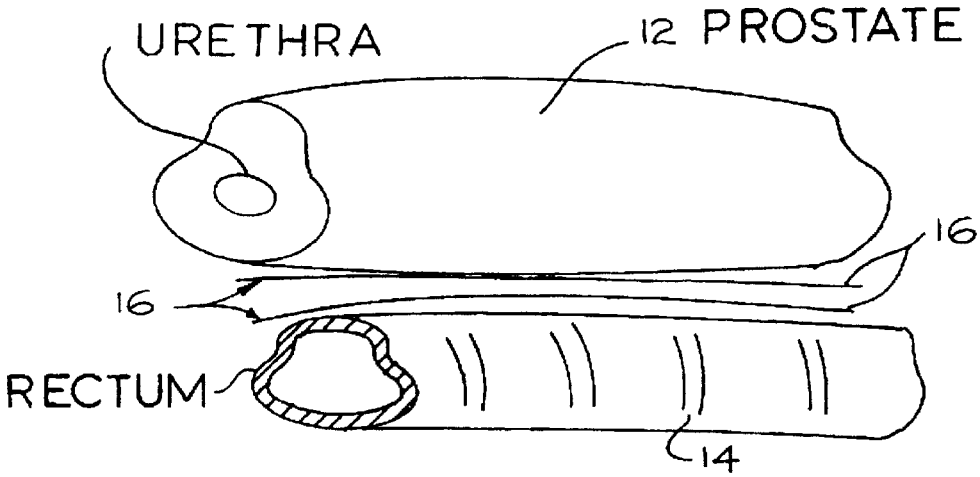
FIG. 1 illustrates a front view of a human prostate and rectum in accordance with conventional medical knowledge.
Figure 2:
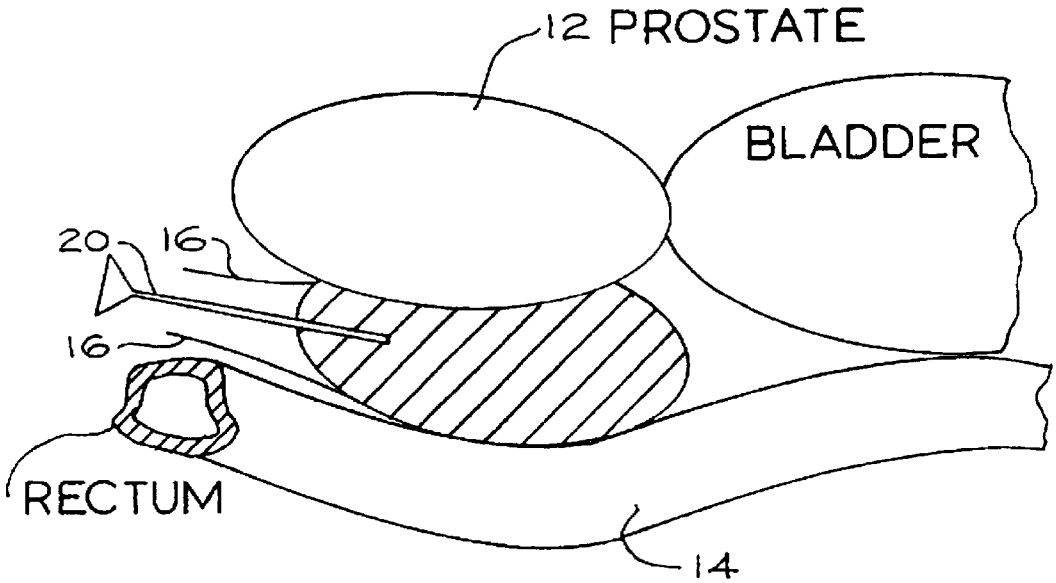
FIG. 2 shows a front view of the prostate and rectum of FIG. 1 physically separated by a fluid.
Figure 3:
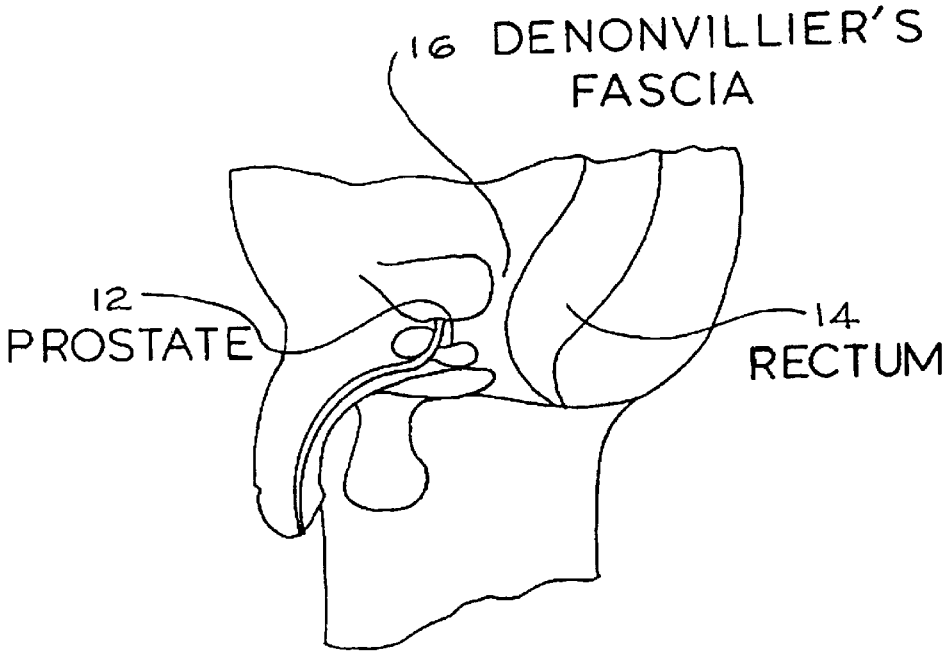
FIG. 3 illustrates a side view of a prostate and rectum physically separated by a fluid.
Figure 4:
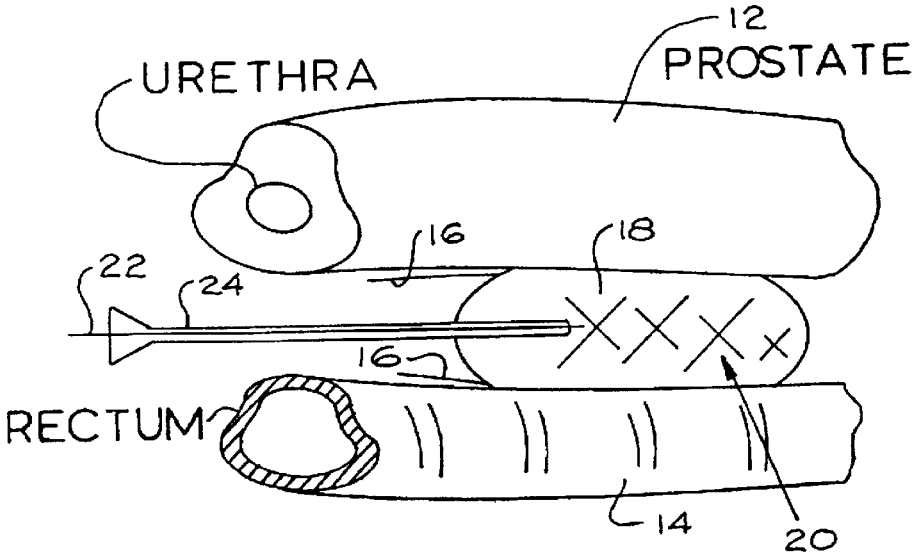
FIG. 4 shows a front view of the prostate and rectum of FIG. 2 showing a device for providing the fluid and a fluid temperature sensor.

FIG. 1 illustrates a front view of a human prostate 12 located immediately above a human rectum 14 in accordance with well known anatomical observations. The prostate and the rectum 14 are separated by a thin facial plane called "Denoviller's fascia" or a "biplane fascial layer" 16. Denoviller's fascia is composed of two layers of fibrous membrane tissue in close contact. To kill prostatic cancer cells within the prostate 12, the entire prostate 12 must typically be subjected to the thermal therapy, regardless of whether heating or cooling techniques are utilized. Because the rectum 14 naturally lies in intimate contact with the prostate 12 and the biplane fascial layer 16, if one subjects the periphery of the prostate 12 to intense thermal therapy to kill all living tissue within, one risks damaging the portions of the rectum 14 close to the prostate 12. Such damage can lead to serve complications such as urethral or vesicle-rectal fistulae.

The present invention can be ultrasound or magnetic resonance or other imaging modalities to direct the percutaneous (through trans-perineal techniques or others) instillation of fluid 18 under pressure into the biplane fascial layer 16 (Denovillers fascia) to create a real space 20 from the pre-existing virtual space, thereby physically separating the rectum 14 from the prostate 12. Extremely low fluid pressures (i.e., gravity-fed flows) can be used in accordance with the invention if desired. The fluid 18 tracks into this fascial plane, physically and thermally isolating the rectum 14 from the prosate 12, and isolating the prostate 12 from lateral and inferior lying structures (e.g., the perineal diaphragm, sphincteric mechanism and neurovascular bundles). Fluid 18 can be continuously instilled to cool (or warm, as desired) and separate this space 20 and protect adjacent structures. Thermoprobes can be placed into the periphery of the prostate to ensure adequate temperatures to ablate cancer cells while temperature sensors 22 and pressure monitors in the fluid space can dictate the amount of fluid flow necessary to adequately protect adjacent structures. Conventional intermittent trans-rectal ultrasound can also help ensure adequate continuing separation of vital tissues by the instilled cooling fluid 18.

In accordance with one preferred embodiment of the invention, a needle 24 is inserted at a location near or between the prostate 12 and rectum 14 to infuse a fluid 18 for cleaving or providing a space 20 physically separating the prostate 12 and rectum 14. It will be apparent that all of the organ separation methods described herein can be practiced from a variety of entry ports: transperineally, transrectally, transurethrally, suprapubically and others. The fluid 18 can be a cooling solution (ionic or nonionic), an insulating medium (as in energy absorption), an energy reflecting medium for use with some trans-urethral therapy applications, a warming solution, air or a gas, or some type of gel. Infusing these types of agents essentially provides a space 20 to either help insulate the rectum 14 from the therapy or can provide a means to either augment the therapy or to provide the actual therapy itself.

The fluid 18 can be bolused in or continuously infused to provide proper maintenance of the space 20 between the organs and proper temperature of the fluid 18. The fluid 18 can also be recirculated into and out of the space 20 by the use of a multilumen catheter or by use of multiple catheters. For heat treatments, the fluid 18 can be cooled to provide cooling to the rectum 14. Alternatively, the fluid 18 can be maintained at a minimally therapeutic temperature. Therefore, monitoring of the fluid 18 temperature within the space 20 or in the delivered and returned solution temperature can be used to guide or enhance the treatment of effectiveness. For cooling or freezing treatments of the prostate 12, the fluid 18 can be warmed to ensure that the rectum 14 is provided a safety cushion such that the therapy inside the prostate 12 can be as aggressive as possible.

In accordance with another form of the invention, a mechanical separator 28 can be utilized to provide this space 20 and remove the need to infuse or continuously infuse an agent which would either be resorbed by the body or withdrawn by a physician.

This space 20, once created, can also be used to provide a window within which to now deliver therapy, feedback regarding the extent of the treatment by providing more localized control or for various types of imaging (e.g., ultrasound). Further details for implementing those functionalities are described hereinbelow. This technique can be especially useful for prostate cancer which develops predominantly in the posterior and lateral edges of the prostate 12. The close proximity of the thermally sensitive rectum 14 to those commonly afflicted areas of the prostate 12 limits the effectiveness of conventional treatment. By utilizing the space 20 or window to now provide a means for directly treating these regions of the prostrate 12 in a directional way, the rectum 14 can be protected from thermal damage, and the location of the cancer can be extremely aggressively treated in a safe and relatively comfortable manner. Therapy elements (energy sources) capable of providing desirably asymmetric energy patterns include, without limitation, laser, microwave (especially with some type of shielding (e.g., air) to avoid heating the rectum 14), cryosurgery, ultrasound (focused or diffuse) and diagnostic ultrasound. The diagnostic ultrasound and the therapeutic ultrasound can be combined into the same probe if desired.

Figure 5:
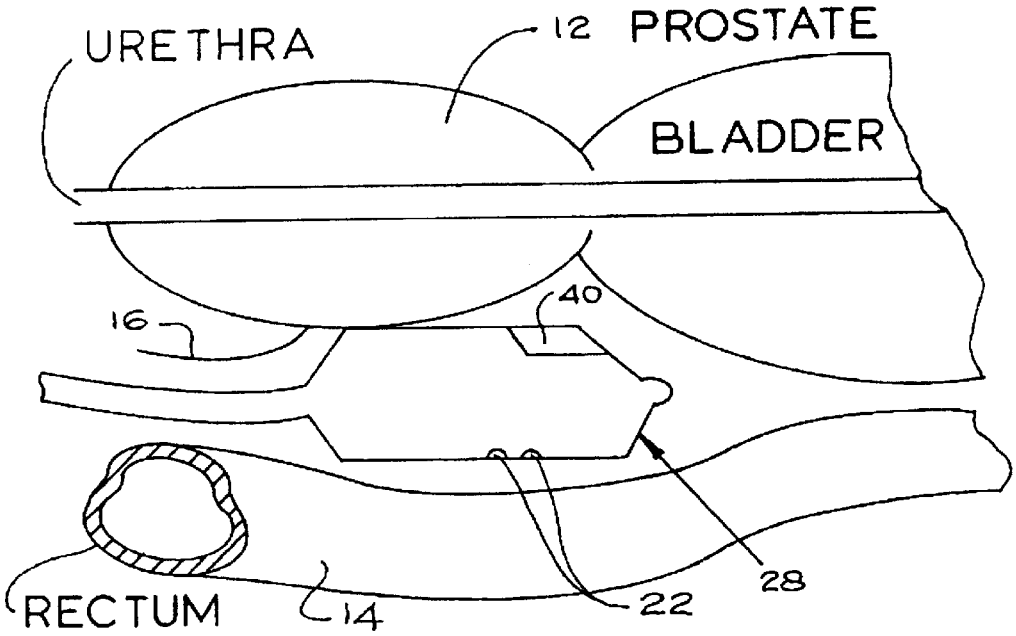
FIG. 5 illustrates a front view of a prostate and rectum separated by a mechanical separator including a thermotherapy delivery system.
Figure 6:
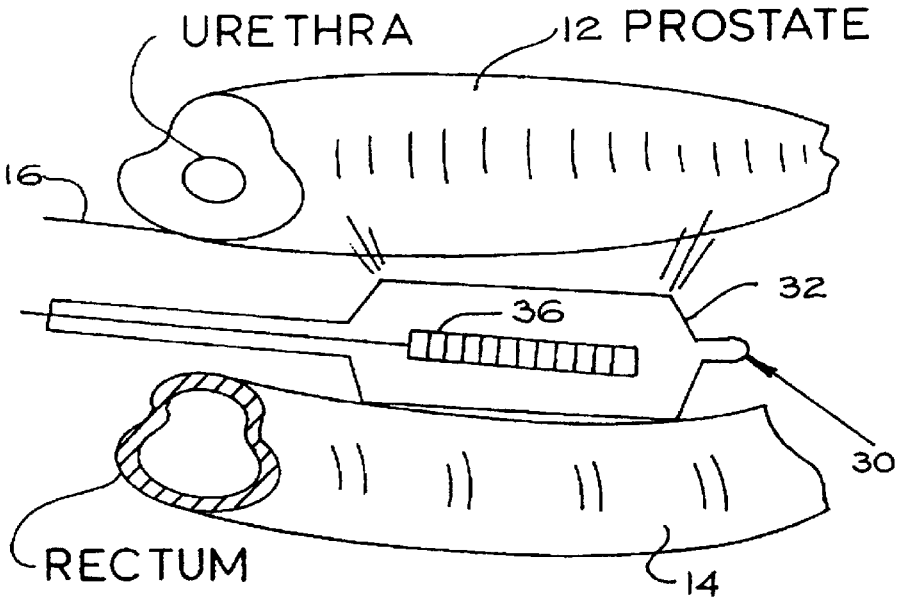
FIG. 6 shows a side view of the prostate, rectum and mechanical separator of FIG. 5.
Figure 7:
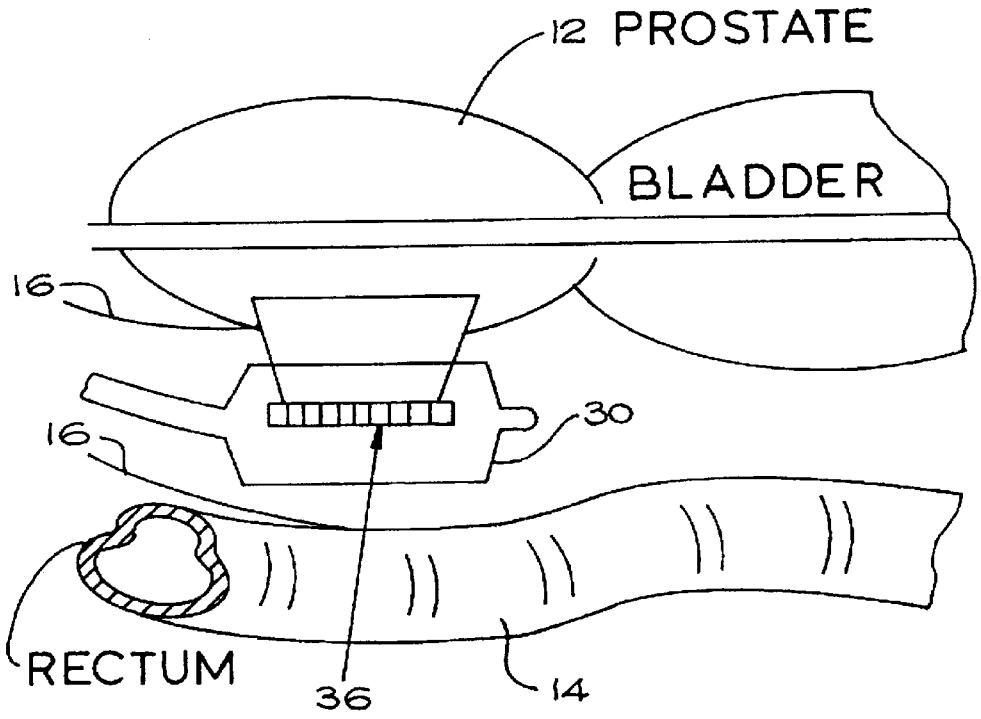
FIG. 7 illustrates a side view of the prostate, rectum and mechanical separator of FIG. 5 and 6 showing thermal therapy application to the prostate.

Suitable mechanical separators 28 can comprise a variety of configurations and materials. For instance, a conventional balloon catheter 30 can be inserted into the biplane fascial layer 16 and inflated to lift the prostate 12 away from the rectum 14 as shown in FIGS. 5 and 6. Further, any number of mechanical devices can be used such as graspers, expanders, and similar devices. The balloon catheter 30 can be inflated with air, water, gel or virtually any other fluid, and the fluid 18 can be either static or continuously recirculated. Alternatively, open-ended devices can be used to both partially or completely physically separate and instill fluid. The fluid can be selected to cool the therapeutic element 36 and help separate the organs. It will be apparent to one of ordinary skill in the art that air or other fluids that do not freeze should be used for freezing types of thermal therapy treatments.

The balloon 32 can include a nondistensible or infinitely expandable (i.e., latex) structure for creating the desired space 20. The temperature of the inner portion of the balloon 32 can be monitored and regulated to a specified temperature. This temperature can also be modified during a treatment to suit the individual clinical/therapeutic needs or targets. In this way, either warming or cooling can be administered as the need arises. This temperature can also be used to ensure that the (peripheral) outer portions of the prostate 12 achieve a desired thermal therapy treatment temperature while ensuring that the rectum 14 remains at safe, subtherapeutic temperatures.

Temperature sensors 22 can also be added to the outside of the separator 28 in various locations including, but not limited to, along the base of the prostate 12 and/or along the rectal wall. In this way, more direct monitoring of anatomical structures of interest can be achieved and all tissues can be maintained at desired temperatures. The separator 28 can also provide a mechanism for treating the outer portions of the gland as discussed hereinafter.

For example, the separator 28 can also be used to house a therapeutic element 36 such as one or multiple lasers, therapeutic ultrasound (focused, directional or diffuse), diagnostic ultrasound or microwave elements. The therapeutic element 36 can be directional, shielded or simply conventional. The element 36 can then be used to effectively treat the outer portions of the prostate 12. This approach can be used in conjunction with another form of treatment, either drug or device, and can be used with interstitial or intraluminal treatments. If needed, a conventional endoscope or similar device can be inserted to guide the application of the treatment under direct visualization.

The therapeutic element 36 can incorporate a locating means 40 whereby the location of the treatment can be confirmed, adjusted or maintained throughout the treatment. This locating means 40 can include, without limitation, a helium neon laser pointer for direct vision or a mechanical/ultrasoun opaque (i.e., metal) indicator on the probe itself. It can also comprise an ultrasound imaging device capable of monitoring the therapeutic effect in the tissue itself.

While prostate treatment uses of the present invention are described herein for illustrative purposes, it will be readily apparent that the present invention can also be used to treat other anatomical structures including, without limitation, structures inherent or attached to the rectum 14 itself (e.g., treating the wall of the rectum 14 or tumors associated with the rectum 14).

Figure 8:
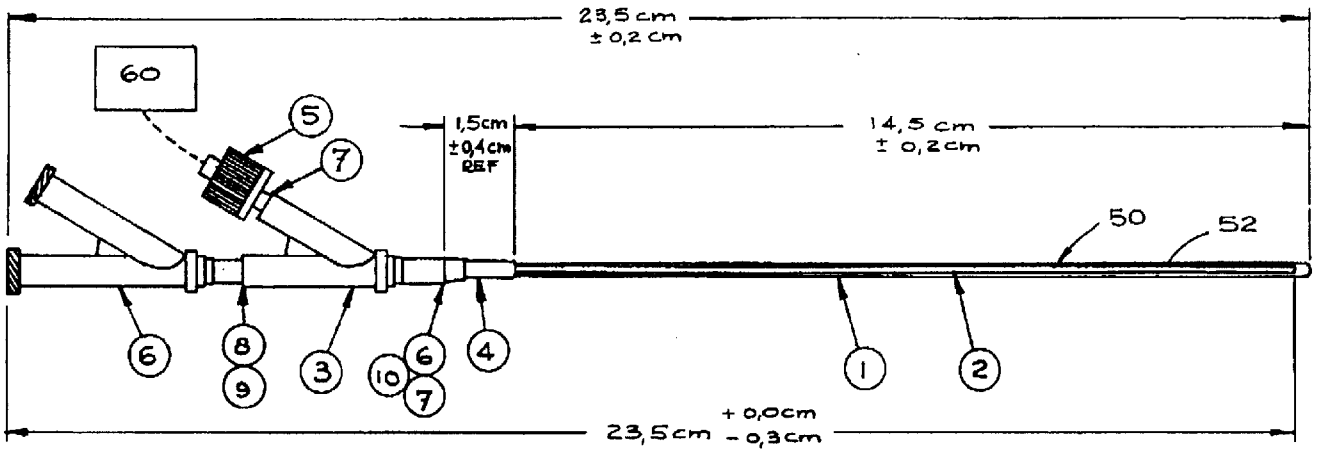
FIG. 8 shows a front view of a delivery system constructed in accordance with one form of the invention.

Thermal therapy delivery systems 50 can also be used as mechanical separators 28. The delivery system 50 can take a number of forms, such as the one described in co-pending U.S. patent application Ser. No. 07/976,232, the Detailed Description of Preferred Embodiments which is incorporated herein in its entirety. Alternatively, the delivery system 50 shown in FIG. 8 can be used satisfactorily. The delivery system 50 can include the ability to provide degassed and temperature regulated water flow into the delivery system 50 adjacent tissue to be treated. An example of such a suitable delivery system 50 is a single or multiple lumen device which circulates fluid, gas, gel and the like under pressure within a closed environment. The delivery system 50 is intended to be inserted into body cavities or interstitially. The delivery system 50 can be inserted into the body (organ) targeting a specific treatment site. The delivery system 50 can house a therapeutic element 36 such as laser, microwave, therapeutic or diagnostic ultrasound or simply a temperature sensor 22. The fluid 18 or infused agent can be recirculated under pressure or can remain static. This form of the invention can deliver therapeutic energy to internal body structures through a minimally invasive procedure.

The delivery system 50 is preferably small in diameter, being 9 French and under. Delivery system 50 as small as 6 French have been used satisfactorily and are being further miniamrized. The delivery system 50 incorporates 360 degree radial cooling (or warming) which is essential for this intensive thermal therapy, especially for interstitial therapy, because it greatly reduces the potential for exit wounds which could result from both thermal or freezing technologies.

The delivery system 50 can be made out of extremely thin polymers, such as PET, which permits the use of very thin wall thicknesses, thereby minimizing the overall device size. This type of material is essentially nondistensible and can withstand high pressures without failure. This permits passage of fluid 18 or other media under pressure to provide flow without compromise of the structure. The delivery system 50 can also be made from typical catheter materials with the size increasing due to the need for larger wall thicknesses.

The delivery system 50 can have a rigid structure that aids in insertion or could be made so thin that it essentially has no rigidity. The latter design can be inflated to provide the handling and insertion stability required. This has the advantage of permitting extremely thin wall thicknesses to be used, thereby, maximizing throughput flow and/or minimizing overall size. The rigidity of the delivery system 50 can also be used in conjunction with a conventional sharpened tip at one end of the delivery system 50. The sharpened tip enables interstitial insertion of the delivery system 50 where desired.

The circulating fluid 18 could be either a cooling agent or a warming agent, whichever is required for the particular thermal therapy being utilized. For example, microwave therapy benefits from a cooled device whereby the cooling of the antenna provides a substantial increase in efficiency. The delivery system 50 preferably incorporates the therapeutic elements 36 with complete cooling or warming (via submersion) along the therapeutic element's 36 entire length. This configuration is the most efficient use of space, thereby resulting in a smaller profile.

The outer structure (lumen) 52 of the delivery system 50 can be made either nondistensible or moderately to fully distensible. A distensible outer lumen diameter can be changed even during a treatment to maintain desired contact with the surrounding tissue. This is important for therapies that benefit from intimate contact between the applicator and the tissue for efficient transmission of energy such as microwave, laser, ultrasound and the like.

The change in lumen 52 diameter can be accomplished via an active increase in the internal pressure of the delivery system 50. The pressure can be increased (inflated), decreased or otherwise controlled automatically (or manually) and triggered via the recording or reflected or lost power transmission which can be monitored real time. A conventional pump 60 or other inflation system can be controlled electronically for this purpose. This can be a feedback circuit to improve the efficient transmission of energy throughout the duration of the treatment. In this way, intimate contact between the delivery system 50 and the surrounding tissue can be maintained throughout the treatment, increasing the efficiency of the energy transmission.

Pressurization can also be a useful feature of the delivery system 50 for: clearing the pathway of air or impurities; cooling or warming; and reducing or eliminating modifications in the environment resulting from the treatment. For example, in microwave treatments, the cooling medium is typically a deionized solution such as distilled water. With the application of microwave energy, the microbubbles are produced along the antenna resulting in an increase in reflected power. This can develop into an almost total stoppage of emitted energy into the tissue. Pressurization desirably changes the degassing characteristics of the medium and can minimize the effect of microbubbles on energy transmission. Flowing fluid 18 also washes any of the microbubbles out of the energy emitting pathway. Air will block the transmission of most energy sources such as microwave and ultrasound. Laser will also see this as another interface which can result in overheating of the delivery system 50 in that region possibly resulting in delivery system 50 or laser malfunction. Pressurization can therefore reduce or eliminate reflected power and can be varied throughout a treatment to compensate for changes in the reflected power levels that may occur.

Reflected power will also change according to the matching/mismatching characteristics of the environment surrounding the delivery system 50. This is especially true for microwave energy. Therefore, the measurement of reflected power can be used to correlate with tissue changes in the surrounding tissue. This measurement can, therefore, be used as a feedback mechanism for the progression of a treatment or for a regulating mechanism during a treatment. It can be used as a surrogate measure of tissue temperature, or tissue destruction and can also be used to determine if the treatment is being applied too aggressively. For example, if the therapy is too aggressive, the interface between the delivery system 50 and the surrounding tissue may change (e.g., dehydrate) which will impact the matching between the two entities. The severity of the mismatch will be reflected in an increase in the reflected power. This mismatch clinically results in a less effective administered treatment. By reacting to the change in the reflected power, the aggressiveness of the treatment can be modified to manage this event. Reflected power will change with changes in the temperature of the environment surrounding the delivery system 50. Accordingly, this measure can be used to estimate the temperature of the environment. This is the same for actual physical changes in the surrounding environment (e.g., denaturization, carbonization, dehydration, etc.); therefore this measure can also estimate effects of a treatment upon the surrounding environment.

While preferred embodiments have been illustrated and described, it should be understood that changes and modifications can be made therein without departing from the invention in its broader aspects. Various features of the invention are defined in the following claims.

We claim:

1. A method of providing thermal to prostate tissue of a patient, comprising the steps of:

inserting a fluid infusing device into the patient;

locating the fluid infusing device at a location adjacent a portion of the patient's prostate and the patient's rectum to provide passage of a volume of a fluid from the device to said location without a containment structure between the portion of the patient's prostate and the rectum, said location selected to allow said fluid to begin physically separating the portion of the prostate and the rectum;

continuing to infuse said fluid causing physical separation of the portion of the prostate and the rectum; and applying said thermal therapy to the prostate tissue.

2. The method as defined in claim 1, further including the step of containing to infuse said fluid to completely physically separate all portions of the prostate and the rectum with said fluid.

3. The method as defined in claim 1, wherein said location is disposed in a biplane fascial layer of the patient.

4. The method as defined in claim 1, including the step of delivering the fluid under pressure.

5. The method as defined in claim 1, including the step of using a recirculating apparatus to recirculate said fluid.

6. The method as defined in claim 1, and including the step of positioning the temperature sensor to be disposed in contact with said fluid.

7. The method as defined in claim 1, wherein said fluid cools the rectum.

8. The method as defined in claim 1, wherein said fluid is a liquid.

9. A method of providing thermal therapy to prostate tissue of a patient, comprising the steps of:

providing a gel to a location adjacent a portion of the patient's prostate and the patient's rectum, said location selected to allow said gel to begin physically separating the portion of the prostate and the rectum;

said gel causing physical separation of the portion of the prostate and the rectum and applying said thermal therapy to the prostate tissue.

10. A method of providing thermal therapy to prostate tissue of a patient, comprising the steps of:

inserting a fluid infusing device into the patient;

locating the fluid infusing device at a location adjacent at a portion of the patient's prostate and the patient's rectum to provide passage of a volume of a fluid from the device to said location without a containment structure between the portion of the patient's prostate and the rectum, said location selected to allow said fluid to begin physically separating the portion of the prostate and the rectum;

continuing to infuse said fluid causing physical separation of the portion of the prostate and the rectum;

applying said thermal therapy to the prostate tissue; and using a temperature sensor to sense temperature of the volume of fluid to minimize damage to the prostate and to the rectum.

* * * * *